United States Patent [19]

Efange et al.

[11] Patent Number: 5,616,575
[45] Date of Patent: Apr. 1, 1997

[54] BIOACTIVE TRICYCLIC IBOGAINE ANALOGS

[75] Inventors: S. Mbua N. Efange, Plymouth, Minn.; Deborah C. Mash, North Bay Village, Fla.

[73] Assignees: Regents of the University of Minnesota, Minneapolis, Minn.; University of Miami, Miami, Fla.

[21] Appl. No.: 567,374

[22] Filed: Dec. 4, 1995

[51] Int. Cl.$^6$ .................................................. A61K 31/395
[52] U.S. Cl. ........................... 514/215; 540/586; 514/812
[58] Field of Search ................................... 514/215, 812; 540/586

[56] References Cited

U.S. PATENT DOCUMENTS

| | | | |
|---|---|---|---|
| 3,714,193 | 1/1973 | Suh | 540/586 |
| 4,499,096 | 2/1985 | Lotsof | 514/214 |
| 4,938,949 | 7/1990 | Borch et al. | 424/10 |
| 5,006,521 | 9/1991 | Lafferty et al. | 514/215 |
| 5,035,878 | 7/1991 | Borch et al. | 424/10 |
| 5,258,378 | 11/1993 | Clark et al. | 514/215 |

FOREIGN PATENT DOCUMENTS

28381  5/1981  European Pat. Off. .

OTHER PUBLICATIONS

S.L.T. Cappendijk et al., "Inhibitory Effects of Ibogaine on Cocaine Self–Administration in Rats," *Eur. J. Pharmacol.*, 241, 261–265 (1993).

D.C. Deecher et al., "Mechanisms of Action of Ibogaine and Harmaline Congeners Based on Radioligand Binding Studies," *Brain Res.*, 571, 242–247 (1992).

G. Di Chiara et al., "Drugs Abused by Humans Preferentially Increase Synaptic Dopamine Concentrations in the Mesolimbic System of Freely Moving Rats," *Proc. Natl. Acad. Sci.*, 85, 5274–5278 (1988).

A.J. Elliot et al., "Synthesis of Some 5–Phenylhexahydroazepino[4,5–b] indoles as Potential neuroleptic Agents," *J. Med. Chem.*, 23, 1268–1269 (1980).

D.M. Gallant et al., "A Controlled Evaluation in Chronic Schizophrenic Patients," *Current Therapeutic Res.*, 9, 579–580 (1967).

S.D. Glick et al., "Local Effects of Ibogaine on Extracellular Levels of Dopamine and its Metabolites in Nucleus Accumbens and Striatum: Interactions with D–Amphetamine," *Brain Res.*, 628, 201–208 (1993).

J.B. Hester et al., "Azepinoindoles. I. Hexahydroazepinol [4,5–b] indoles," *J. Med. Chem.*, 11, 101–106 (1968).

G.F. Koob et al., "Neuroanatomical Substrates of Drug Self–Administration," *The Neuropharmacological Basis of Reward*, Clarendon 214–263 (1989).

E. O'Hearn et al., "Degeneration of Purkinje Cells in Parasagittal Zones of the Cerebellar Vermis after Treatment with Ibogaine or Harmaline," *Neurosci.*, 55, 303–310 (1993).

E. O'Hearn et al., "Ibogaine Induces Glial Activation in Parasagittal Zones of the Cerebellum," *Neuroreport.*, 4, 299–302 (1993).

J.A. Schneider et al., "Neuropharmacological Studies on Ibogaine, an Indole Alkaloid with Central Stimulant Properties," *Ann. NY Acad. Sci.*, 66, 765–776 (1957).

H. Sershen et al., "Ibogaine Reduces Preference for Cocaine Consumption in C57BL/6By Mice," *Pharmacol. Biochem. Behav.*, 47, 13–19 (1994).

G. Singbartl et al., "Structure–Activity Relationships of Intracerebrally Injected Tremorigenic Indole Alkaloids," *Neuropharmacology*, 12, 239–244 (1973).

W.L. Woolverton et al., "Neurobiology of Cocaine Abuse," *Trends Pharmacol. Sci.*, 13, 193–200 (1992).

G. Zetler et al., "Cerebral Pharmacokinetics of Tremor–Producing Harmala and Iboga Alkaloids," *Pharmacology*, 7, 237–248 (1972).

*Primary Examiner*—James H. Reamer
*Attorney, Agent, or Firm*—Schwegman, Lundberg, Woessner & Kluth, P.A.

[57] ABSTRACT

Ibogaine analogs are provided, which are phenyl-substituted-hexahydroazepino[4,5-b]indoles useful to treat cocaine addiction and the use of other addictive substances.

21 Claims, 3 Drawing Sheets

BIOACTIVE TRICYCLIC IBOGAINE ANALOGS

BACKGROUND OF THE INVENTION

While the management of substance abuse has been largely dependent on behavior modification, recent advances in neurochemistry have resulted in a growing realization that a rational pharmacotherapy founded on the neurochemistry of substance dependence may yield significant dividends. Drugs which are characterized by a high abuse liability belong to several structural and pharmacological classes (reviewed in G. DiChiara et al., *PNAS*, 85, 5274 (1988)). Pharmacological classes include central stimulants, central depressants, hallucinogens and narcotic analgesics. Although a similar degree of diversity characterizes the primary sites of action of these agents, recent evidence points to a common underlying mechanism for chemical dependence. For example, the rewarding effects of drugs such as morphine and cocaine have been associated with the preferential activation of the mesolimbic dopaminergic system (for review, see G. F. Koob et al., *The Neuropharmacological Basis of Reward*, Clarendon (1989) at pages 214–263).

On the basis of these observations, it has been suggested that drugs which antagonize the activation of these pathways may be potentially useful in the treatment of chemical dependence. Recent attempts to develop pharmacotherapy for cocaine abuse have focused on the neurochemistry of reward and withdrawal. Although cocaine primarily increases synaptic levels of monoamines, including dopamine, norepinephrine and serotonin, it is believed that repeated exposure to cocaine results in depletion of dopamine (for review, see W. L. Woolverton et al., *Trends Pharmacol. Sci.*, 13, 193 (1992)). Consequently, drug-seeking behavior in the addict is presumed to be motivated by a) the desire to alleviate the unpleasant effects of withdrawal (attributed to dopamine depletion) and b) the desire to experience the pleasurable effects associated with cocaine self-administration.

Consistent with this view, dopamine agonists and antagonists have been proposed for treatment of withdrawal and for antagonizing the positive re-enforcing effects of cocaine. Although this approach presents some intriguing possibilities for the treatment of drug abuse, few clear successes have been reported. While the dopamine hypothesis of drug addiction continues to present a number of intriguing possibilities for the development of a useful pharmacotherapy of cocaine and opiate addiction, it is clear from these preliminary investigations that direct blockade of dopamine receptors may not be the most suitable pharmacological approach. Given the multiplicity of dopamine receptor subtypes and the absence of corresponding selective ligands, the final judgment on the viability of this approach may be not reached for a long time. In the interim, the need to pursue alternative leads remains unabated.

Ibogaine is the major constituent of the root of *Tabernanthe iboga*, a naturally occurring shrub commonly found in West and Central Africa. The structure is shown in FIG. 1(A). Pharmacological evaluation of this agent in dogs and rabbits revealed unusual excitatory effects and local anesthetic activity. In a later evaluation of ibogaine as a potential phrenotropic agent, J. A. Schneider et al., *Ann. NY Acad. Sci.*, 66, 765 (1957) confirmed that ibogaine was a psychostimulant which caused phobia, ataxia and tremors in cats.

The anti-addictive effects of ibogaine were first reported by drug addicts seeking new psychoactive agents. Administration of ibogaine was followed by a period of hallucinations (lasting several hours), followed by a longer cognitive phase of intense introspection. At the end of this period, some addicts reported alleviation or cessation of craving, and a few remained drug-free for several years thereafter. Although these earlier reports were anecdotal, a method for the treatment of cocaine and opiate abuse based on ibogaine was subsequently patented by Lotsoff in 1985 (U.S. Pat. No. 4,499,096). Subsequent investigation of ibogaine in rodents and monkeys has prompted the initiation of limited human trials. A marked reduction in cocaine self-administration is evident in some animals after a single dose of this compound. However, other animals required up to three doses to exhibit comparable effects (S. D. Glick et al., *Brain Res.*, 628, 201 (1994)). Similarly, ibogaine was effective in reducing craving in some humans while others were unaffected.

Despite the positive results in animals, the clinical utility of ibogaine may be severely limited. Ibogaine apparently interacts with a diverse number of molecular targets (J. C. Deecher et al., *Brain Res.*, 571,242 (1992)). This multiplicity of active sites is manifested in vivo in a number of undesirable side-effects. Specifically, ibogaine (and related compounds) are hallucinogenic (J. A. Schneider et al., *Ann. NY Acad. Sci:*, 66, 765 (1957)), tremorigenic (G. Zetler et al., *Pharmacology*, 7, 237 (1972); G. Singbartl et al., *Neuropharmacol.*, 12, 239 (1973)) and, at higher doses, excitotoxic (E. O'Hearn et al., *NeuroReport*, 4, 299 (1993), E. O'Hearn et al., *Neurosci.*, 55, 303 (1993)).

Ibogaine analogs formally based on fragmentation of the parent compound have also been prepared and, in some cases, investigated for bioactivity. S. D. Glick et al., *Brain Res.*, 628, 201 (1993) (FIG. 1(C)) recently reported that the ibogaine analogs R-ibogaine (FIG. 1(B)) and R-coronaridine (FIG. 1(C)) reduced dopamine levels in the nucleus accumbens and striatum.

The substructure 1,2,3,4,5,6-hexahydroazepino[4,5-b]indole (FIG. 1(D)) and some of its derivatives were synthesized years ago as a means of restraining the conformational mobility of the aminoethyl fragment of tryptamine (J. B. Hester et al., *J. Med. Chem.*, 11, 101 (1968)). One of these compounds, 6-methyl-1,2,3,4,5,6-hexahydroazepino[4,5-b]indole was found by Hester et al. to antagonize aggressive behavior in fighting mice, block conditioned avoidance, and induce hypothermia and anorexigenic behavior in rodents. However, the compound did not exhibit neuroleptic activity in humans (D. M. Gallant et al., *Current Therapeutic Res.*, 9, 579 (1967)). In a subsequent report, A. J. Elliott et al., *J. Med. Chem.*, 23, 1268 (1980) described a series of 5-phenyl-1,2,3,4,5,6-hexahydroazepino[4,5b]indoles. In mice, these compounds failed to exhibit neuroleptic activity. However, two analogues, 5-phenyl-1,2,3,4,5,6-hexahydroazepino[4,5-b]indole and 3-methyl-5-phenyl-1,2,3,4,5,6-hexahydroazepino[4,5-b]indole, displayed antidepressant activity. The antidepressant properties of these analogues are reminiscent of ibogaine. The synthesis of 2-alkyl-1,2,3,4,5,6-hexahydroazepino[4,5-b]indoles has been reported in the patent literature (Gadient, EPA, 28,381 (1981)). However, no biological data were provided.

Therefore, a need exists for the preparation and characterization of bioactive ibogaine analogs, particularly those useful to treat substance abuse, i.e., cocaine or opiate addiction.

SUMMARY OF THE INVENTION

The present invention provides a series of ibogaine analogs of formula (I):

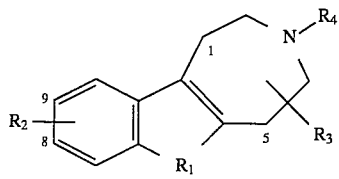

wherein $R_1$ is S or O;

$R_2$ is H, $(C_1-C_4)$alkyl, $(C_1-C_4)$alkoxy OH, CN, $CONH_2$, halo, oxazolyl, $(C_1-C_4)$alkylS, or $(C_1-C_2)$trifluoroalkyl;

$R_3$ is a phenyl group optionally substituted at the 2'- or 3'-position of the phenyl ring with halo, $N(R)_2$, wherein each R is H or $(C_1-C_4)$alkyl; or $NO_2$; and $R_4$ is $(C_3-C_6)$cycloalkyl$(C_1-C_4)$alkyl $(C_3-C_6)$cycloalkyl or $(C_1-C_4)$alkyl, optionally containing 1-2 double bonds, and the pharmaceutically acceptable salts thereof.

The ring numbering system is that of FIG. 1(D). The stereochemistry of the $R_3$ group may be alpha (below the plane of the ring), beta (above the plane of the ring), or a mixture thereof. As drawn in formula (I), the $R_2$ can occupy any open position on the benzyl ring and the $R_3$ group can occupy any position on the azepine ring, preferably the 4- or 5-position. Optically pure enantiomers (R- or S-) are within the scope of formula (I), as well as racemic RS-mixtures.

Preferably, $R_2$ is in the 8- or 9-position and $R_3$ is at the 5-position. Preferably, $R_1$ is S and $R_3$ is 3'-substituted. $(C_1-C_4)$alkyl is preferably methyl.

The present invention also provides pharmaceutical compositions comprising one or more compounds of formula (I) in combination with a pharmaceutically acceptable carrier, which compositions may be in the form of unit dosage forms adapted for oral or parenteral administration.

The present invention also provides a method to treat addiction to, or use of, chemicals such as narcotic analgesics including opiates (heroin, morphine), other addictive analgesic mu-receptor agonists (fentanyl, demerol, etc.) psychostimulants, (cocaine and its analogs), central depressants, and hallucinogens (DMT, mescaline, MDA, LSD) by administering to a human in need of such treatment, an effective amount of a compound of formula (I). Preferably, the treatment reduces the craving (drug-seeking), tolerance and/or reinforcing properties associated with the use of addictive substances, such as cocaine.

The present compounds can also exhibit some of the isolated bioactivities of ibogaine, including anti-depressant, anti-motor, anti-anxiolytic, anesthetic, tranquilizer, and anorexigenic activities, at pharmacologically useful levels, without exhibiting the neurotoxicity tremorigenic, excitotoxic activity, or other undesirable effects of ibogaine.

DETAILED DESCRIPTION OF THE INVENTION

Figure 1A:
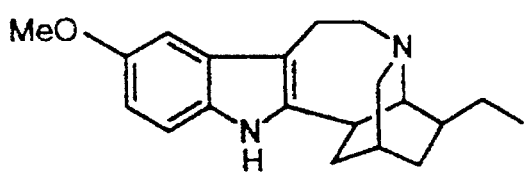
FIG. 1 depicts the structures of ibogaine (A), R-ibogamine (B), R-coronaridine (C), 1,2,3,4,5,6-hexahydroazepino[4,5-b]indole (D), 7a (E), 7b (F), 7c (G).
Figure 1B:
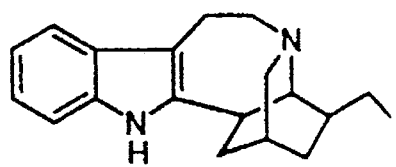
Figure 1C:
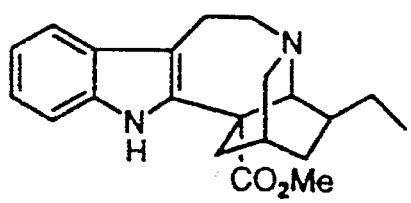
Figure 1D:
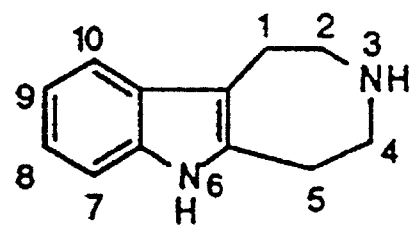
Figure 1E:
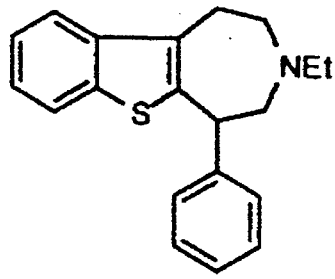
Figure 1F:
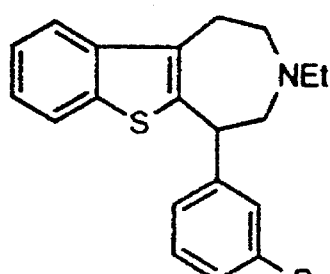
Figure 1G:
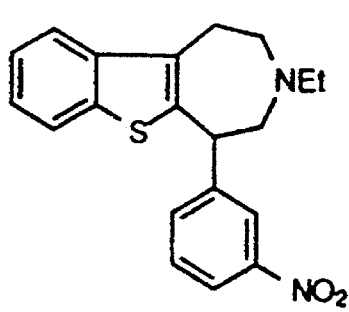
Figure 2:
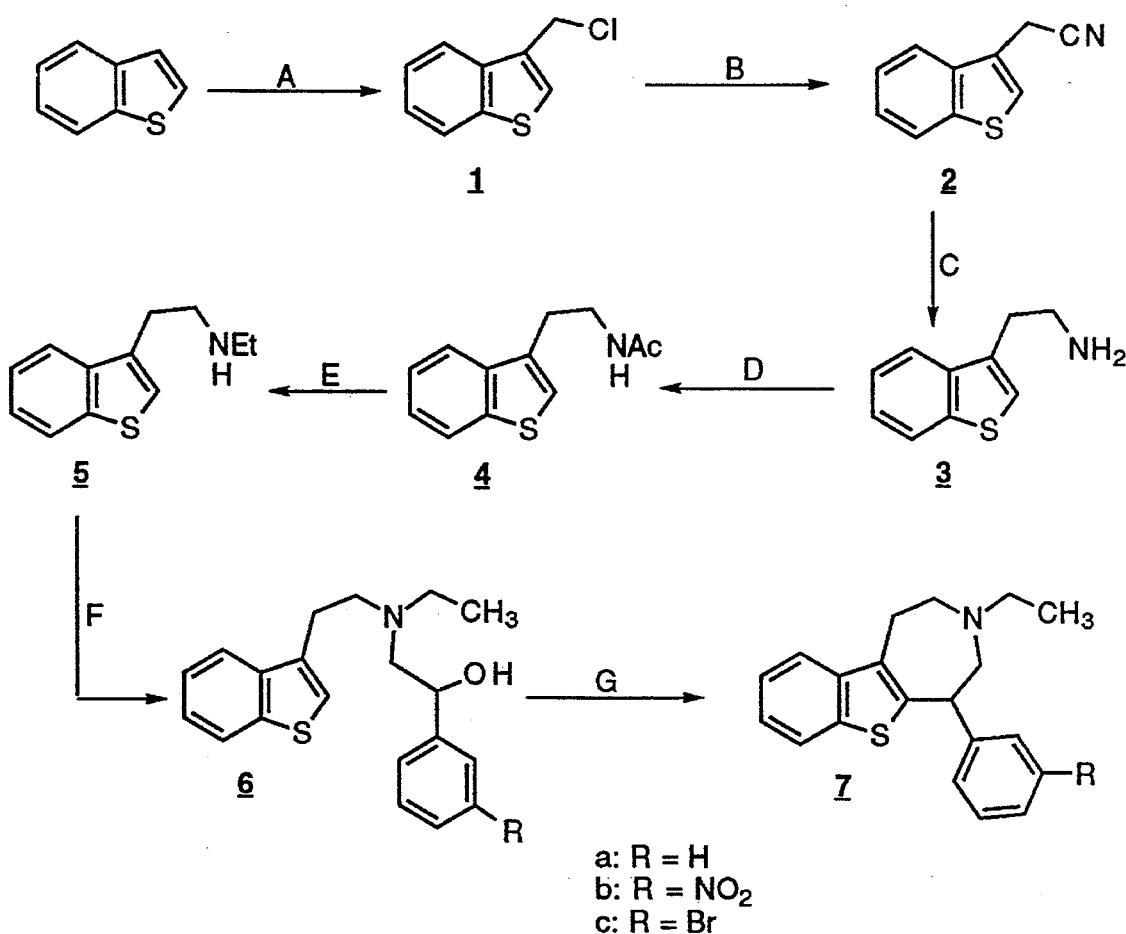
FIG. 2 depicts the synthesis of compounds 7a (R=H), 7b (R=$NO_2$), and 7c (R=Br) wherein A: $CH_2O$ (aq.), HCl(g), conc. HCl; B: KCN, PTC, $H_2O$, 90°–95° C.; C: $LiAlH_4$, $AlCl_3$, reflux; D: $Ac_2O$, $Et_3N$; E: $BH_3 \cdot THF$, reflux; F: styrene oxide, reflux; G: $CF_3CO_2H$, cone. $H_2SO_4$(cat.).

The synthesis of ibogaine analogs 7a–c is outlined in FIG. 2, wherein the benzo[b]thiophene is chloromethylated to yield 1, then reacted with cyanide ion to yield 3-cyanomethylbenzothiophene (2), which is reduced with $LiAlH_4$/$AlCl_3$ to yield the corresponding primary amine 3. The latter was acetylated with acetic anhydride and the resulting amide was reduced with borane-tetrahydrofuran to yield 5. Refluxing of the 5 with a preselected styrene oxide in EtOH and subsequent cyclization of the corresponding secondary alcohol provided the compounds 7a, (R=H) 7b (R=$NO_2$) and 7c (R=Br). The compounds were characterized by $^1H$ NMR and purity was determined by combustion analysis. Cyclization was associated with a 0.1δ upfield shift in the methine proton signal. The hydrochlorides were prepared by passing HCl gas through a solution of the corresponding free bases in EtOH.

Other compounds of formula (I) (or 7) can be readily prepared by employing various 6- or 7-substituted benzothiophenes or benzofurans in the reaction scheme of FIG. 1, followed by reaction of compound 5 or the corresponding benzofuran with readily available phenyl-substituted styrene oxides. Alternatively, 2'- or 3'-substituted compounds of formula (I) (or 7) can be converted to different phenyl ring substituents by reactions known to the art, including reduction of nitro groups to amines, alkylation of amines, halogenhalogen exchange, or hydrolysis or amidation of halides or the corresponding lithio or Grignard reagents to yield OH, alkoxy, amino or aminoalkyl groups.

Resolution of acemates may be accomplished by (a) conversion to the corresponding ureas, followed by chromatographic separation of the diasteriomers, (b) chromatographic separation on a chiral column, or (c) fractional crystallization of the diasteriomeric tartarates or quinidine salts.

Pharmaceutically acceptable amine salts of these compounds may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. These physiologically acceptable salts are prepared by methods known in the art, e.g., by dissolving the free amine bases with an excess of the acid in aqueous alcohol.

In the clinical practice of the present method, the compounds of the present invention will normally be administered orally or parenterally, as by injection or infusion, in the form of a pharmaceutical preparation comprising the active ingredient in combination with a pharmaceutically acceptable carrier, e.g., in the form of a pharmaceutical unit dosage form. The carrier may be a solid, semi-solid, or liquid diluent or be compressed or shaped into an ingestible capsule. The compound or its salt may also be used without carrier material.

Examples of pharmaceutical unit dosage forms comprising the present antagonists include tablets, preselected volumes of intravenous solutions, suspensions, hard or soft gelatin capsules, microcapsules, suppositories, liposomes and systems designed for controlled or prolonged release of the active agent, such as biodegradable microparticles or reservoirs designed for transdermal delivery or subcutaneous delivery. Such reservoirs include skin patches and shaped polymeric implants.

Usually, the active substance will make up between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration. Oral doses of about 0.5–50 mg/kg/day can be employed in the present method.

Doses of a given compound of formulas I, II or III which are effective to counteract the use of addictive substances, such as cocaine, including cocaine salts or analogs can be extrapolated, to some extent, from the murine data by methods known to the art for extrapolation of animal dosing data to humans. For example, see U.S. Pat. Nos. 5,035,878 and 4,938,949.

There are a number of germane bioassays for measuring the bioactivity of the present compounds. These include (a) tests using guinea pig ileal longitudinal muscle (GPI), (b) tests using mouse vas deferens (MVD), and those indexing behavior of mice or rats which include, (c) writhing associated with injections of irritants, (d) conditioned place preference (CPP) tests, (e) tests using rewarding brain stimulation and (f) drug self-administration tests. Each of these methods are widely used by practitioners of the art, because information derived from these bioassays predict responsiveness in human beings. See, for example, S. L. T. Cappendijk et al., *Eur. J. Pharmacol.*, 241, 261 (1993); H. Sershen et al., *Pharmacol. Biochem. Behavior*, 47, 13 (1934).

The invention will be further described by reference to the following, detailed examples, wherein synthetic intermediates were purchased from Aldrich Chemical Company, Inc. (Milwaukee, Wis.) and Lancaster Synthesis (Windham, Mass.), and were used as received. Solvents are distilled immediately before use.

Standard handling techniques for air-sensitive materials were employed throughout. Preparative chromatography was performed on a Harrison Research Chromatotron using Merck 60 PH254 silica gel. Analytical TLC was performed on Analtech GHLF silica gel plates, and the chromatograms were visualized by UV and/or methanolic iodine. Melting points were determined on a Mel-Temp melting point apparatus and are uncorrected. $^1$H NMR spectra were recorded on an IBM Brucker spectrometer at 200 MHz. NMR spectra are referenced to the deuterium lock frequency of the spectrometer. Under these conditions, the chemical shifts (in ppm) of residual solvent in the $^1$H NMR spectra are found to be as follows: $CHCl_3$, 7.26; DMSO, 2.56; HOD, 4.81. The following abbreviations are used, where appropriate, to describe the peak splitting patterns: br=broad, s,=singlet, d=doublet, t=triplet, q=quartet, m=multiplet. Both low- and high-resolution mass spectrometry were performed on an AEI MS-30 instrument. Elemental analyses were performed by Atlantic Microlab, Inc., Norcross, Ga.

EXAMPLE 1

3-(Chloromethyl)benzo[b]thiophene (1)

HCl (g) was bubbled vigorously through a mixture of thianaphthene (17.0 g, 126.68 mmol), 37% aq. formaldehyde (15 mL) and conc HCl (15 mL) until the reaction temperature rose to 65° C. At this time, the flow of HCl gas was reduced to a slow stream which was maintained for 1.5 hour. The reaction mixture was diluted with $H_2O$ (50 mL) and subsequently extracted with ether (2×50 mL). The combined ethereal extracts were dried over $Na_2SO_4$ and concentrated under reduced pressure to yield 1 as a straw colored liquid 21.0 g (90.7%). $^1$H NMR ($CDCl_3$) $\delta$4.90 (s, 2, $CH_2$—$C_1$), 7.25 (s, 1, CH—S), 7.45 (m, 2, phenyl), 7.88 (m, 2, phenyl).

EXAMPLE 2

3-(Cyanomethyl)benzo[b]thiophene (2)

Potassium cyanide (6.65 g, 102.14 mmol) and benzyl triethylammonium chloride (23.26 g, 227.78 mmol) were dissolved in $H_2O$ (50 mL) in a round-bottomed flask fitted with a stirrer, reflux condenser and a dropping funnel. 3-(Chloromethyl)thianaphthene (15.0 g, 82.12 mmol) was added dropwise with cooling (water bath) to the well stirred mixture, and the resulting emulsion was heated at 90°–95° C. for 1 h. The reaction mixture was diluted with water (50 mL) and extracted with $CH_2Cl_2$ (2×50 mL). The organic extracts were combined, dried over $Na_2SO_4$ and concentrated to a residue. The crude product was purified by radial flow chromatography [hexane (9):acetone (1)] to obtain 4.0 g (28%) of 2 as a pale colored crystalline solid. $^1$H NMR ($CDCl_3$) $\delta$3.69 (s, 2, $CH_2$—$C_1$), 7.25–7.91 (m, 5, phenyl, CH—S).

EXAMPLE 3

5 2-(Benzo[b]thien-3-yl)ethylamine(3)

To a stirred slurry of lithium aluminum hydride (1.16 g, 30.32 mmol) in dry ether (50 mL) was added, under $N_2$, a slurry of aluminum chloride (4.04 g, 30.32 mmol) in dry ether (50 mL). After 5 min, a solution of 3-(cyanomethyl)thianaphthene (5.25 g, 30.32 mmol) in ether (50 mL) was slowly added over 10 min. Upon completion of the addition, the resulting mixture was refluxed for 22 h, cooled, neutralized with a 20% aq. solution of Rochelle's salt and extracted with ethyl acetate (3×100 ML). The combined organic extracts were dried over $Na_2SO_4$ and concentrated under reduced pressure to yield the amine as a syrup. The corresponding amine hydrochloride was obtained by treating the free base 3 with a solution of methanolic HCl; yield of hydrochloride, 4.61 g (71%). $^1$H NMR ($CDCl_3$) $\delta$1.43 (s, 2, —$NH_2$), 3.00 (m, 4, —$CH_2$—$CH_2$—), 7.11 (s, 1, CH—S), 7.36 (m, 2, phenyl), 7.72–7.86 (m, 2, phenyl).

EXAMPLE 4

2-(Benzo[b]thien-3-yl)ethyl acetamide (4)

2-(Benzo[b]thien-3-yl)ethylamine (0.75 g, 4.23 mmol) was dissolved in DMF (5 mL) and 5 equivalents of $Ac_2O$ and 3 equivalents of $Et_3N$ were added. The mixture was stirred for 18 h at room temperature, diluted with $H_2O$ (25 mL) and extracted with $CH_2Cl_2$ (2×25 mL). The organic extracts were dried over $Na_2SO_4$ and concentrated to a residue to provide 0.88 g (94%) of 4 as a viscous liquid. $^1$H NMR ($CDCl_3$) $\delta$1.88 (s, 3, —CH3), 3.00(m, 2, —$C\underline{H}_2$—), 3.54 (m, 2, $CH_2$—NH), 6.29 (br s, 1, NH), 7.10 (s, 1, CH—S), 7.25–7.37 (m, 2, phenyl), 7.72–7.86 (m, 2, phenyl).

EXAMPLE 5

N-2-(Benzo[b]thien-3-yl)ethyl-N-ethylamine (5)

Compound 4 (0.85 g, mmol) was refluxed in 1M BH$_3$.THF (20 ml) for 18 h. Upon cooling, the reaction mixture was acidified with 2N HCl (20 ml). The mixture was adjusted to pH 8 with 2N NaOH (aq.) and partitioned between water and CH$_2$Cl$_2$ (50 mL). The CH$_2$Cl$_2$ extracts were dried over Na$_2$SO$_4$ and concentrated under reduced pressure to yield a residue which was refluxed in 6N HCl for 6 h. Finally, the resulting mixture was cooled to room temperature, made alkaline by treatment with NaOH pellets and extracted with CH$_2$Cl$_2$ (2×50 mL). The combined organic extracts were dried over Na$_2$SO$_4$ and concentrated to provide 0.52 g (65%) of the product 5 as a syrup. $^1$H NMR (CDCl$_3$) δ1.09 (t, 3, J=7 Hz, —CH$_3$), 2.68 (q, 2, J=7 Hz, CH$_3$—CH$_2$—), 2, C$\underline{H}_2$—NH), 3.63 (t, J=6 Hz, 2, C$\underline{H}_2$, —CH$_2$—NH), 6.29 (br s, 1, NH), 7.15 CH—S), 7.25–7.39 (m, 2, phenyl), 7.75–7.88 (m, 2, phenyl).

EXAMPLE 6

N-[2-(Benzothien-3-yl)ethyl]-N-ethyl-N-[2-hydroxy-2-phenylethylamine (6a)

A mixture of compound 5 (0.50 g, 2.44 mmol) and styrene oxide (0.32 g, 2.93 mmol) was refluxed in EtOH (5 mL) for 3 h. The reaction mixture was concentrated under reduced pressure and the crude product was purified by radial flow chromatography [hexane(9):acetone(1)] to yield 0.32 g (43%) of 6a as a pale yellow oil. $^1$H NMR (CDCl$_3$) δ1.17 (t, 3, —CH$_3$), 2.26–3.08 (m, 8, all methylene protons), 4.44 (br s, 1, —OH), 4.66 (dd, 1, C$\underline{H}$—OH), 7.17 (s, 1, CH—S), 7.46 (m, 7, phenyl), 7.76–7.91 (m, 2, phenyl).

EXAMPLE 7

3-Ethyl-5-phenyl-1,2,3,4,5-pentahydroazepino[4,5-b]benzothiophene (7a)

Compound 6a (0.30 g, 1 mmol) was refluxed in CF$_3$COOH (5 mL) in the presence of H$_2$SO$_4$ (100 mL) for 3 h. The reaction mixture was diluted with water (10 mL), adjusted to pH 8 with solid NaHCO$_3$, and extracted with EtOAc (2×50 mL). The EtOAc extracts were dried over Na$_2$SO$_4$ and concentrated under reduced pressure to obtain the free amine as a yellow oil. The latter was converted to the corresponding hydrochloride with methanolic HCl and recrystallized from i-PrOH-ether to yield 160 mg (57%) of 7a as a yellowish brown solid. $^1$H NMR (CDCl$_3$) δ1.10 (t,3, J=7 Hz, C$\underline{H}_3$–CH$_2$—), 2.77 (q, 2, J=7 Hz, CH3—CH$_2$—), 2.80 (m, 2, azepinyl), 3.20 (m, 4, azepinyl), 4.49 (dd, 1, Ph$_2$—CH—), 7.19–7.67 (m, 9, phenyl).

Anal. (C$_{20}$H$_{21}$NS.HCl.H$_2$O) Calc: C, 66.37; H,6.68; N, 3.87. Found: C, 66.45; H, 6.53; N,3.71.

EXAMPLE 8

3-Nitrostyrene oxide

A solution of 3-nitrostyrene (1.0 g, 6.70 mmol) in CH$_2$Cl$_2$ (10 mL) was cooled in an ice bath. 3-Chloroperoxybenzoic acid (57% pure) (2.23 g, 7.38 mmol) was added in one batch and the stirring was continued for 18 h. The reaction mixture was concentrated to a residue and diluted with CCl$_4$ (20 mL). Precipitated m-chlorobenzoic acid was removed by filtration and the filtrate was washed with a 50:50 mixture of 5% aq. NaHCO$_3$ and 5% aq. NaHSO$_3$ (100 mL). The organic extract was dried over Na$_2$SO$_4$ and concentrated under reduced pressure to yield 0.70 g (64%) of a yellow oil. $^1$H NMR (CDCl$_3$) δ2.81 (m, 1, CH), 3.20 (m, 1, CH—), 3.97 (m, 1, —CH—), 7.62 (m, 2, phenyl), 8.16 (m, 2, phenyl).

EXAMPLE 9

3-Bromostyrene oxide

A solution of 3-bromostyrene (1.0 g, 5.46 mmol) in CH$_2$Cl$_2$ (10 mL) was cooled in an ice bath. 3-Chloroperoxybenzoic acid (57% pure) (1.82 g, 6.01 mmol) was added in one batch and the stirring was continued over 18 h. The reaction mixture was concentrated to a residue and diluted with CCl$_4$ (20 mL). Precipitated m-chlorobenzoic acid was removed by filtration and the filtrate was washed with a 50:50 mixture of 5% aq. NaHCO$_3$ and 5% aq. NaHSO$_3$ (100 mL). The organic extract was dried over Na$_2$SO$_4$ and concentrated under reduced pressure to yield 0.80 g (64%) of product as a yellow oil. $^1$H NMR (CDCl$_3$) δ2.74 (m, 1, CH), 3.14 (m, 1, CH—), 3.82 (m, 1, —CH—), 7.21 (m, 2, phenyl), 7.42 (m, 2, phenyl).

EXAMPLE 10

N-[2-(Benzothien-3-yl,)ethyl]-N-ethyl-N-[2-hydroxy-2-(3-nitrophenyl]ethylamine (6b)

A mixture of compound 5 (0.79 g, 3.84 mmol) and 3-nitrostyrene oxide (0.69 g, 4.23 mmol) was refluxed in EtOH (5 mL) for 3 h. The reaction mixture was concentrated under reduced pressure and the crude product was purified by radial flow chromatography [5:1, hexane(5)-acetone(1)] to yield 0.66 g (46%) of 6b as a pale yellow oil. $^1$H NMR (CDCl$_3$) δ1.22 (t, 3, CH$_3$), 2.14–3.60 (m, 8, all methylene Hs), 4.64 (br s, 1, OH—), 4.66 (dd, 1, CH—OH), 7.14 (s, 1, CH—S), 7.30–8.25 (m, 8, phenyl).

EXAMPLE 11

N-[2-(Benzothien-3-yl)ethyl]-N-ethyl-N-[2-hydroxy-2-(3-bromophenyl]ethylamine (6c)

Compound 5 (2.4 g, 11.69 mmol) and 3-bromostyrene oxide (2.56 g, 12.86 mmol) was refluxed in EtOH (10 mL) for 3 h. The reaction mixture was concentrated under reduced pressure to yield the crude product which was purified by radial flow chromatography [5:1, hexane(5)-acetone(1)] to provide 1.40 g (30%) of 6c as a pale yellow oil. $^1$H NMR (CDCl$_3$) δ1.14 (t, 3, CH$_3$), 2.23–3.16 (m, 8, all methylene Hs), 4.05 (br s,1, OH), 4.55 (dd,1, CH—OH), 7.15 (s, 1, CH—S), 7.18–7.80 (m, 8, phenyl).

EXAMPLE 12

3-Ethyl-5-(3-nitrophenyl)-1,2,3,4,5-pentahydroazepino[4,5-b]benzothiophene (7b)

Compound 6b (0.66 g, 1.87 mmol) was refluxed in CF$_3$COOH (5 mL) in the presence of H$_2$SO$_4$ (100 mL) for 3 h. The reaction mixture was concentrated to a residue which was neutralized with satd NaHCO$_3$ and extracted with CH$_2$Cl$_2$ (2×25 mL). The CH$_2$Cl$_2$ extracts were dried over Na$_2$SO$_4$ and concentrated to a residue which was chromatographed [5:1, hexane(5):acetone(1)] to yield 0.3 g (46%) of the product. The hydrochloride, obtained by treatment of the free base with methanolic HCl, was recrystallized from i-PrOH:ether to obtain 7b as a straw colored solid. $^1$H NMR (CDCl$_3$) δ1.08 (t, 3, J=7 Hz, C$\underline{H}_3$—CH$_2$—), 2.74 (q, 2, J=7 Hz, CH3—CH$_2$—), 2.94 (m, 2, azepinyl), 3.11 (m, 4, azepinyl), 4.55 (dd,1,Ph$_2$CH), 7.25–8.27 (m, 8, phenyl).

Anal. C$_{20}$H$_{21}$N$_2$O$_2$S.HCl.3/4H$_2$O. Calc: C,59.69; H,5.71; N,6.95. Found: C,59.60; H,5.53; N,6.85.

EXAMPLE 13

3-Ethyl-5-(3-bromophenyl)-1,2,3,4,5-pentahydroazepino[4,5-b]benzothiophene (7c)

Compound 6c (1.40 g, 3.46 mmol) was refluxed in $CF_3COOH$ (5 mL) in the presence of $H_2SO_4$ (100 mL) for 3 h. The reaction mixture was concentrated to a residue which was neutralized with satd $NaHCO_3$ and extracted with $CH_2Cl_2$ (2×25 mL). The organic extracts were dried over $Na_2SO_4$ and concentrated to a residue which was chromatographed [5:1, hexane(5):acetone(1)]to yield 0.91 g (65%) of 7c as the product. The hydrochloride was obtained in the same manner described above. $^1H$ NMR ($CDCl_3$) $\delta$1.08 (t, 3, J=7 Hz, C$\underline{H}_3$—$CH_2$—), 2.74 (q, 2, J=7Hz, $CH_3$—$CH_2$—), 2.84 (m, 2, azepinyl), 3.14 (m, azepinyl), 4.42 (dd,1,$Ph_2$—CH), 7.20–7.69 (m, 8, phenyl). Elem. Anal. $C_{20}H_{21}BrNS·HCl·H_2O$. Calc: C, 54.49; H, 5.21; N, 3.17. Found: C,54.69; H,5.06; N,3.04.

EXAMPLE 14. PHARMACOLOGICAL EVALUATION

Figure 3A:
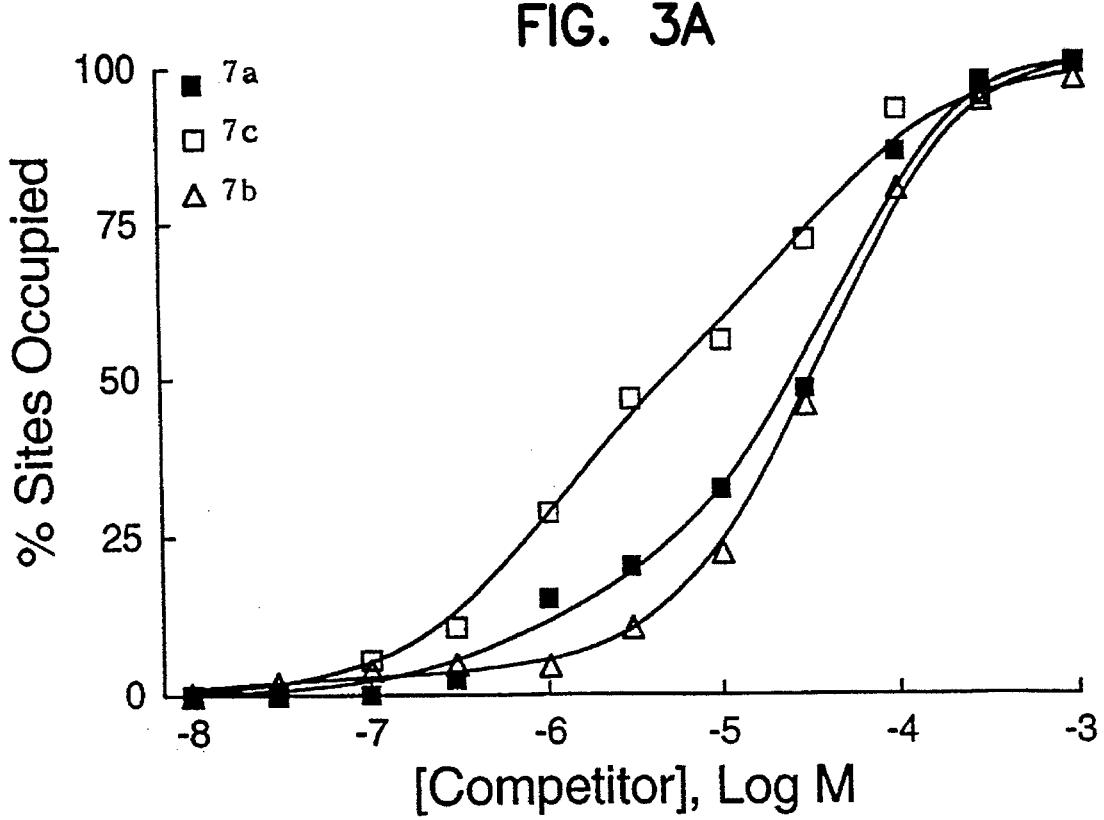
FIG. 3 depicts the binding of 7a (■), 7c (□), and 7b (▲) to the NMDA receptor in human brain tissue from the caudate (A) and cerebellum (B).
Figure 3B:
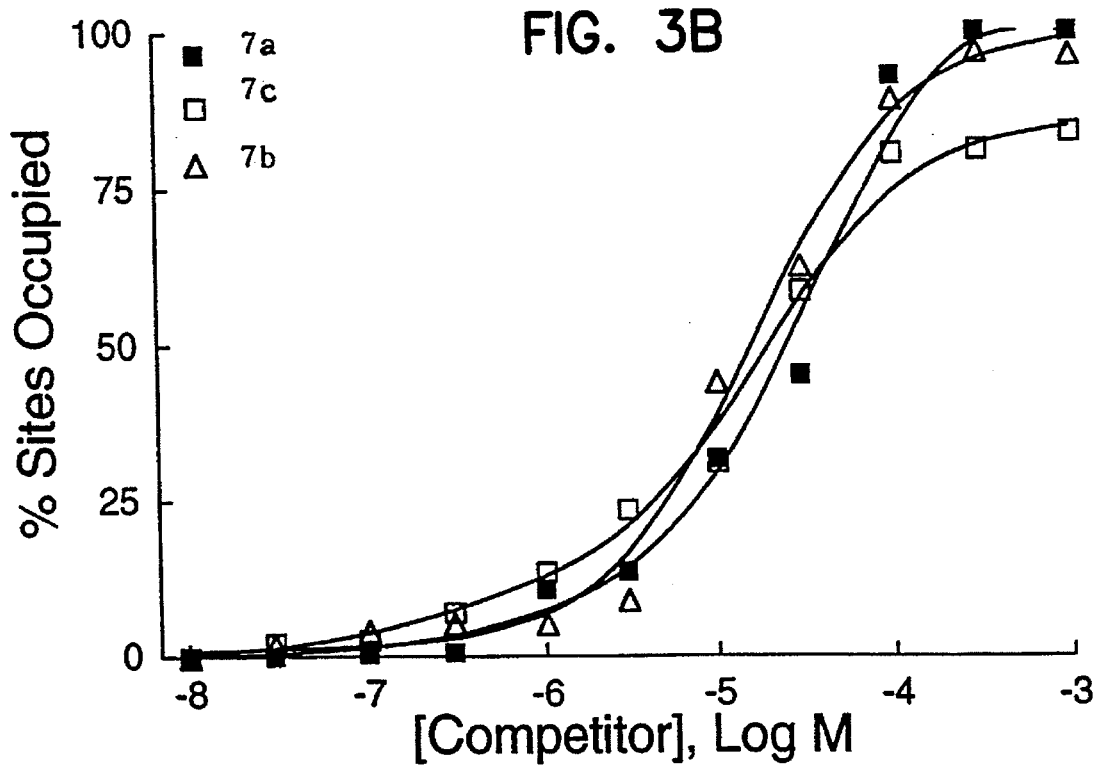

A. In vitro Studies:

The affinity of compounds 7a–c for the NMDA receptor was measured in human brain tissue employing the methodology of P. Popik et al., *Psychopharmacol.*, 114, 672 (1994). As shown in FIG. 3, all three compounds displayed micromolar affinity for the NMDA site in human caudate. However, compound 7c was equipotent with ibogaine and about fivefold more potent than 7a,b and noribogaine. Ibogaine and 7c were also of comparable potency in the cerebellum.

To assess the potential addiction-interrupting effects of the newly synthesized iboganoids, compounds 7a,b,c were tested for binding at the 5-HT transporter and the kappaol and kappa-2 opiate receptors, molecular targets known to modulate mesolimbic dopaminergic function. In preliminary screening experiments, all three compounds were found to be active ($IC_{50}$<10 μM at the 5-HT transporter) but inactive (i.e. $IC_{50}$>10 μM) at the kappa-2 receptor. Moreover, 7a and 7c showed some activity at the kappa-1 receptor whereas 7-b displayed poor affinity for this site.

On the basis of these results, full competition experiments were performed to provide additional structure-activity information. As shown in Table 1, compounds 7a and 7b were two- to threefold more potent than ibogaine at the 5-HT transporter, while the third analogue, 7c, was essentially equipotent with the naturally occurring compound.

TABLE 1

Relative potencies of ibogaine, noribogaine (12-hydroxyibogamine) and synthetic iboganoids at the 5-HT transporter in human occipital cortex[a].

| Compound | $IC_{50}$, μM | nH |
|---|---|---|
| Ibogaine | 0.59 ± 0.09 | 0.80 ± 0.1 |
| Noribogaine | 0.039 ± 0.0004 | 0.78 ± 0.06 |
| 7a | 0.21 ± 0.01 | 1.0 ± 0.1 |
| 7b | 0.26 ± 0.06 | 1.0 ± 0.2 |
| 7c | 0.82 ± 0.16 | 1.2 ± 0.2 |

[a]Membranes isolated from human occipital cortex were incubated for 1 hr at 25° C., in the presence of 1 μM benztropine, with 0.01 nM [$^{125}$I]RTI-55 and varying concentrations of the respective compounds. Data analysis was performed with EBDA (DRUG). The data presented are the mean ± S.D. of two independent determinations conducted in triplicate, non-specific binding was evaluated using 50 μm (-)-cocaine. (See, J.K. Staley et al., J. Neurochem., 62, 549 (1994)).

However, ibogaine and all three synthetic ibogonoids were at least one order of magnitude less potent than noribogaine. At the kappa-1 receptor (Table 2), noribogaine was sixfold more potent than ibogaine. Of the two synthetic ibogonoids, 7a and 7c, the former was found to be essentially equipotent with ibogaine while the latter was significantly less potent.

TABLE 2

Relative potencies of Ibogaine, noribogaine and synthetic ibogonoids at the kappa-1 receptor of human insular cortex.[a]

| Compound | $IC_{50}$, μM | nH |
|---|---|---|
| Ibogaine | 25 ± 0.57 | 1.1 ± 0.1 |
| Noribogaine | 4.24 ± 0.28 | 1.1 ± 0.1 |
| 7c | | |
| (NS = 10 μM Naloxone) | 117.06 ± 14.50 | 0.6 ± 0.1 |
| (NS, Computer-derived) | 48.99 ± 0.96 | 0.9 ± 0.1 |
| 7a | | |
| (NS = 10 μM Naloxone) | 17.19 ± 3.18 | 0.5 ± 0.0 |
| (NS, Computer-derived) | 10.12 ± 2.01 | 1.3 ± 0.1 |

[a]Membranes isolated from human insular cortex were incubated for 1 hr at 25° C. with 0.3 nM [$^3H$]U693593 and varying concentrations of the respective compounds. See R.B. Rothman et al., Peptides, 13, 977 (1992); B. Nock et al., Eur. J. Pharmacol., 154, 27 (1988). Data analysis was performed with EBDA (DRUG); NS = nonspecific binding. The data presented are the mean ± S.D. of two independent determinations conducted in triplicate.

Taken together, the foregoing provide additional evidence that the hexahydroazepinoindoles of the invention (and related bioisosteric fragments) can retain many of the biological properties associated with ibogaine, including the critical elements for recognition at the 5-HT transporter and the kappa opiate receptor.

B. In vivo evaluation: Rats treated with 7a (100 μmol/kg) showed severe reduction in locomotor activity and ataxia. Breathing appeared labored and the tail remained outstretched and limp. Onset of symptoms was evident within 2 minutes, and the effects were most severe by 5 min. Signs of recovery became evident by 40 min post-injection and the animals appeared fully recovered after 60 min. Mild tremors were observed between 3 and 8 min post-injection. Similar effects were noted following the injection of a comparable dose of compound 7b. However, no tremors were observed.

At 10 mg/kg ip, cocaine (injected 10 min after 7b) reversed the reduction in locomotor activity induced by 7b. Similar symptoms were observed with compound 7d; however, a higher dose (150 μmol/kg) was required to achieve these effects. In addition, 7d elicited a moderate degree of retropulsion even at 100 μmol/kg. No effects were observed following the injection of 7c (100 μmol/kg).

Given the similarity between the responses described here and those previously described for ibogaine, it can be concluded that the compounds of formula (I) retain many of the pharmacological properties of ibogaine. Since the locomotor-reducing activity of ibogaine (and its active analogues) may be related to its ability to reduce dopamine levels in the striatum, it is reasonable that compounds 7a,b may also reduce dopamine levels in vivo.

Also, it should be noted that the doses used in this example are only slightly lower than the pharmacologically effective doses of ibogaine (40 mg/kg or 129 μmol/kg). Since at this dose, ibogaine-induced tremors last for up to 3 hours, compounds 7a,b would appear to be much less tremorigenic than ibogaine. Additional studies in the cocaine self-administration model may provide further insights into the pharmacology of these compounds.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the formula (I):

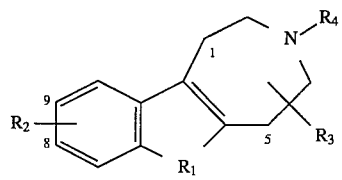

wherein $R_1$ is S or O;

$R_2$ is H, ($C_1$–$C_4$) alkyl, ($C_1$–$C_4$)alkoxy, OH, CN, $CONH_2$, halo, oxazolyl, ($C_1$–$C_4$)alkylthio, or trifluoro($C_1$–$C_2$)alkyl;

$R_3$ is phenyl which is unsubstituted or is substituted at the 2'- or 3'-position of the phenyl ring with halo, $N(R)_2$, wherein each R is $H_2$ or ($C_1$–$C_4$)alkyl; or $NO_2$; and $R_4$ is ($C_3$–$C_6$)cycloalkyl, ($C_1$–$C_4$)alkyl, ($C_3$–$C_6$)cycloalkyl or ($C_1$–$C_4$)alkyl optionally containing 1–2 double bonds.

2. A compound of claim 1 wherein $R_1$ is S.

3. A compound of claim 1 wherein $R_2$ is $CF_3$.

4. A compound of claim 1 wherein $R_2$ is Cl, Br or I.

5. A compound of claim 1 wherein $R_2$ is $CH_3O$.

6. A compound of claim 1 wherein $R_2$ is at the 8- or 9-position.

7. A compound of claim 1 wherein $R_3$ is at the 5-position.

8. A compound of claim 1 wherein $R_3$ is a phenyl group 2'-substituted with Br or $NO_2$.

9. A compound of claim 1 wherein $R_4$ is n-propyl or cyclopropylmethyl.

10. A compound of claim 1 wherein $R_4$ is $CH_3CH_2$—.

11. A compound of claim 2 wherein $R_2$ is H.

12. A compound of claim 11 wherein $R_4$ is $CH_3CH_2$—.

13. A compound of claim 12 wherein $R_3$ is a phenyl group located at the 5-position, where said phenyl group is unsubstituted or substituted with Br or $NO_2$ at the 2'-position of the phenyl group.

14. A compound of claim 13 wherein said phenyl group is substituted with Br.

15. A compound of claim 13 wherein said phenyl group is substituted with $NO_2$.

16. A compound of claim 13 wherein said phenyl group is unsubstituted.

17. A method of treating cocaine use comprising administering to a human in need of such treatment, an amount of a compound of claim 1 effective to reduce the use of cocaine by said human.

18. The method of claim 17 wherein the amount reduces the craving or reinforcing properties associated with cocaine use.

19. A pharmaceutical composition comprising a compound of claim 1 in combination with a pharmaceutically acceptable carrier.

20. The pharmaceutical composition of claim 19 which is adapted for oral administration.

21. The pharmaceutical composition of claim 20 which is adapted for parenteral administration.

* * * * *